(12) United States Patent
Borenstein et al.

(10) Patent No.: US 11,673,094 B2
(45) Date of Patent: Jun. 13, 2023

(54) BIOMIMETIC MICROFLUIDIC DEVICE FOR HIGH EFFICIENCY CARBON DIOXIDE REMOVAL FROM PATIENTS AT LOW BLOOD FLOW RATES

(71) Applicant: The Charles Stark Draper Laboratory, Inc., Cambridge, MA (US)

(72) Inventors: Jeffrey T. Borenstein, Newton, MA (US); Alla A. Gimbel, Medford, MA (US); Jose A. Santos, Westwood, MA (US); James G. Truslow, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 175 days.

(21) Appl. No.: 16/320,897

(22) PCT Filed: May 26, 2017

(86) PCT No.: PCT/US2017/034813
§ 371 (c)(1),
(2) Date: Jan. 25, 2019

(87) PCT Pub. No.: WO2017/205818
PCT Pub. Date: Nov. 30, 2017

(65) Prior Publication Data
US 2019/0184342 A1    Jun. 20, 2019

Related U.S. Application Data

(60) Provisional application No. 62/342,456, filed on May 27, 2016.

(51) Int. Cl.
*B01D 63/08* (2006.01)
*A61M 1/16* (2006.01)
*B01D 69/10* (2006.01)

(52) U.S. Cl.
CPC ......... *B01D 63/088* (2013.01); *A61M 1/1698* (2013.01); *B01D 69/10* (2013.01);
(Continued)

(58) Field of Classification Search
CPC .................. B01D 63/088; B01D 69/10; B01D 2313/146; A61M 1/1698; A61M 2202/0225; A61M 2205/0244
See application file for complete search history.

(56) References Cited

U.S. PATENT DOCUMENTS

| | | | |
|---|---|---|---|
| 4,182,653 A | | 1/1980 | Bellhouse |
| 4,636,310 A | * | 1/1987 | Bellhouse ............ B01D 63/082 210/321.72 |

(Continued)

FOREIGN PATENT DOCUMENTS

| | | |
|---|---|---|
| EP | 0 649 31 A1 | 11/1982 |
| JP | S53-059295 | 5/1978 |

(Continued)

OTHER PUBLICATIONS

Potkay, Joseph, The promise of microfluidic artificial lungs, 2017, Lab on a Chip, Issue 21, pp. 7-9 (Year: 2014).*

(Continued)

*Primary Examiner* — Bradley R Spies
*Assistant Examiner* — Jeannie McDermott
(74) *Attorney, Agent, or Firm* — Foley & Lardner LLP

(57) ABSTRACT

The present disclosure discusses a system and method that includes a microfluidic device that can be used in either an extracorporeal or implantable configuration. The device supports efficient and safe removal of carbon dioxide from the blood of patients suffering from respiratory disease or injury. The microfluidic device can be a multilayer device (Continued)

that includes gas channels and fluid channels. Distensible membranes within the device can affect a cross-sectional area of the blood channels.

20 Claims, 8 Drawing Sheets

(52) U.S. Cl.
CPC ............... *A61M 2202/0225* (2013.01); *A61M 2205/0244* (2013.01); *B01D 2313/146* (2013.01)

(56) References Cited

U.S. PATENT DOCUMENTS

| | | | |
|---|---|---|---|
| 9,180,239 B2 | 11/2015 | Borenstein et al. | |
| 2004/0069717 A1 | 4/2004 | Laurell et al. | |
| 2011/0158847 A1* | 6/2011 | Charest | A61M 1/1698 422/45 |
| 2011/0250585 A1* | 10/2011 | Ingber | G01N 33/5088 435/5 |
| 2011/0290113 A1* | 12/2011 | Borenstein | B01D 63/081 95/54 |
| 2013/0144266 A1* | 6/2013 | Borenstein | A61M 1/1698 604/522 |
| 2014/0193799 A1* | 7/2014 | Borenstein | B01D 63/082 435/2 |
| 2015/0076067 A1* | 3/2015 | Borenstein | B01D 65/08 210/646 |
| 2015/0083320 A1* | 3/2015 | Putnam | B32B 37/0076 156/285 |
| 2015/0306296 A1 | 10/2015 | Borenstein et al. | |
| 2016/0051935 A1* | 2/2016 | Li | B01D 65/02 210/797 |
| 2016/0326477 A1* | 11/2016 | Fernandez-Alcon | B01D 67/0023 |
| 2019/0022294 A1* | 1/2019 | Cho | B01D 53/228 |

FOREIGN PATENT DOCUMENTS

| | | |
|---|---|---|
| JP | 2013-516310 | 5/2013 |
| WO | WO-2013/026148 A1 | 2/2013 |
| WO | WO-2013/086011 | 6/2013 |
| WO | WO-2015/039118 A1 | 3/2015 |
| WO | WO-2015/164618 A1 | 10/2015 |

OTHER PUBLICATIONS

Rodrigues, Carina, et al, Enhancement of mass transfer in spacer-filled channels under laminar regime by pulsatile flow, 2015, Chemical Engineering Science, 123 (2015) 536-541. (Year: 2015).*
Arazawa DT, Kimmel JD, Finn MC, Federspiel WJ. Acidic sweep gas with carbonic anhydrase coated hollow fiber membranes synergistically accelerates $CO_2$ removal from blood. Acta Biomater. Oct. 2015;25:143-9.
Gura, V, Macy, A.S., Beizai M., Ezon C., and Golper, T.A. Technical Breakthroughs in the Wearable Artificial Kidney. Clin J Am Soc Nephrol. Sep. 2009; 4(9): 1441-8.
International Search Report and Written Opinion on PCT/US2017/034813 dated Aug. 17, 2017.
Jeffries RG, Mussin Y, Bulanin DS, Lund LW, Kocyildirim E, Zhumadilov ZZh, Olzhayev FS, Federspiel WJ, Wearden PD. Pre-clinical evaluation of an adult extracorporeal carbon dioxide removal system with active mixing for pediatric respiratory support. Int J Arti Organs. Dec. 2014;37(12):888-99.
Kniazeva T, Epshteyn AA, Hsiao JC, Kim ES, Kolachalama VB, Charest JL, Borenstein JT. Performance and scaling effects in a multilayer microfluidic extracorporeal lung oxygenation device. Lab Chip. May 7, 2012;12(9):1686-95.
Kniazeva T, Hsiao JC, Charest JL, Borenstein JT. A microfluidic respiratory assist device with high gas permeance for artificial lung applications. Biomed Microdevices. Apr. 2011;13(2):315-23.
Lund LW, Federspiel WJ. Removing extra CO(2) in COPD patients. Curr Respir Care Rep. Jun. 28, 2013;2:131-138.
Foreign Action other than Search Report on JP 2018 562220 dated Apr. 6, 2021 with English translation.
Japanese Office on JP Appln 2018-562220 dated Dec. 14, 2021 and English translation thereof (11 pages).
Japanese Office Action on JP Appln. 2018-562220 dated Oct. 18, 2022 and English translation thereof.

* cited by examiner

BIOMIMETIC MICROFLUIDIC DEVICE FOR HIGH EFFICIENCY CARBON DIOXIDE REMOVAL FROM PATIENTS AT LOW BLOOD FLOW RATES

CROSS-REFERENCES TO RELATED APPLICATIONS

This application claims the benefit of priority as a U.S. National Stage under 35 U.S.C. § 371 of International Patent Application No. PCT/US2017/034813, filed on May 27, 2017 and designating the United States, which claims the benefit of and priority under 35 U.S.C. § 119 to U.S. Provisional Patent Application 62/342,456, filed on May 27, 2016. The contents of the foregoing applications are herein incorporated by reference in their entirety for all purposes.

BACKGROUND

Oxygenators can be used as lung assist devices to supplement the oxygenation performed by damaged or diseased lungs. Standard configurations for blood oxygenators are configured to maximize the amount of oxygen transferred to the blood without consideration for maximizing the removal of carbon dioxide within the blood.

SUMMARY OF THE DISCLOSURE

The present disclosure discusses a system and method that includes a microfluidic device that can be used in either an extracorporeal or implantable configuration. The device supports efficient and safe removal of carbon dioxide from the blood of patients suffering from respiratory disease or injury. In some implementations, the microfluidic device is configured to remove clinically relevant rates of carbon dioxide from the blood as the blood flows through the microfluidic device at low blood flow rates. The low blood flow rates can increase safety and blood health. The increased safety can enable the device to be used with patients suffering from acute respiratory distress syndrome (ARDS), chronic obstructive pulmonary disease (COPD), and other diseases that lead to hypercapnia.

According to one aspect of the disclosure a microfluidic flow device can include a first layer. The first lay can include a plurality of gas channels. The device can include a distensible membrane coupled with the first layer. The device can include a second layer. The second layer can include a plurality of blood channels. The second layer can be coupled with the distensible membrane. The plurality of blood channels can be separated from the plurality of gas channels by the distensible membrane. The plurality of blood channels can include a cross-sectional area defined in the second layer. A shape of the cross-sectional area can oscillate along a length of the plurality of blood channels.

The device can also include an inlet manifold that is coupled with an inlet of each of the plurality of blood channels. The device can include an outlet manifold that is coupled with an outlet of each of the plurality of blood channels. The plurality of gas channels can include an open inlet end and an open outlet end.

The device can include a pressure vessel. The pressure vessel can house the first layer and the second layer. The pressure vessel can be configured to flow a gas into an open end of each of the plurality of gas channels. The shape of the cross-sectional area can be controlled by a degree of distension of the distensible membrane. The distensible membrane can be configured to deform a distance responsive to a gas pressure of a gas in the plurality of gas channels.

The device can include a plurality of ribs supporting the distensible membrane. The distensible membrane can deflect toward a central axis of the blood channel between each of the plurality of ribs.

The plurality of ribs can be distributed evenly along the length of the plurality of gas channels. In other implementations, the plurality of ribs can be distributed unevenly along the length of the plurality of gas channels. The distensible membrane can include the plurality of ribs.

According to another aspect of the disclosure, a method can include providing a microfluidic device. The device can include a first layer. The first layer can include a plurality of gas channels. The device can include a distensible membrane coupled with the first layer. The device can include a second layer. The second layer can include a plurality of blood channels. The second layer can be coupled with the distensible membrane. The plurality of blood channels can be separated from the plurality of gas channels by the distensible membrane. The plurality of blood channels can have a cross-sectional area defined in the second layer. The method can include flowing blood through into an inlet of each of the plurality of blood channels. The method can include oscillating a shape of the cross-sectional area along a length of the plurality of blood channels by pressurizing, with a gas, the plurality of gas channels to distend the distensible membrane. The method can include collecting the blood from an outlet of each of the plurality of channels.

The method can also include flowing the blood through an inlet manifold coupled with the inlet of each of the plurality of blood channels. The method can include collecting, from an outlet manifold coupled with the outlet of each of the plurality of blood channels, the blood. The method can include flowing the gas into an open inlet end of the plurality of gas channels.

In some implementations, the method can include pressurizing a pressure vessel housing the microfluidic device. The method can include flowing the gas through the plurality of gas channels with a pulsatile flow. The shape of the cross-sectional area is controlled by a degree of distension of the distensible membrane.

The distensible membrane is configured to deform a distance responsive to a gas pressure of the gas in the plurality of gas channels. The method can include distending the distensible membrane between a plurality of ribs. The plurality of ribs can be distributed evenly along the length of the plurality of gas channels. The ribs are distributed unevenly along the length of the plurality of gas channels. The distensible membrane can include the plurality of ribs. The gas can be air.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

As an overview, this present disclosure describes a microfluidic device which can have a biomimetic flow design. The design supports high efficiency carbon dioxide removal from the blood at very low blood flow rates. Enhanced safety can arise from the reduced reliance on anticoagulants and the reduction in clotting and bleeding relative to current approaches.

The high transfer rates of blood gases are achieved by utilizing thin, gas-permeable membranes, by controlling the gas flow rate and gas composition through the microfluidic device, by controlling the blood channel design to enhance mixing and reduce the build-up of boundary layers, or any combination thereof.

Unlike oxygenation, carbon dioxide removal at clinically relevant rates can be achieved at very low blood flow rates. For example, in some implementations, the present device can achieve the removal of between about 60 mL/min and about 100 ml/min of carbon dioxide at blood flow rates of about 350 mL/min and about 450 mL/min. In contrast, meaningful oxygenation in an adult human may require blood flow rates of several liters per minute.

Figure 1A:
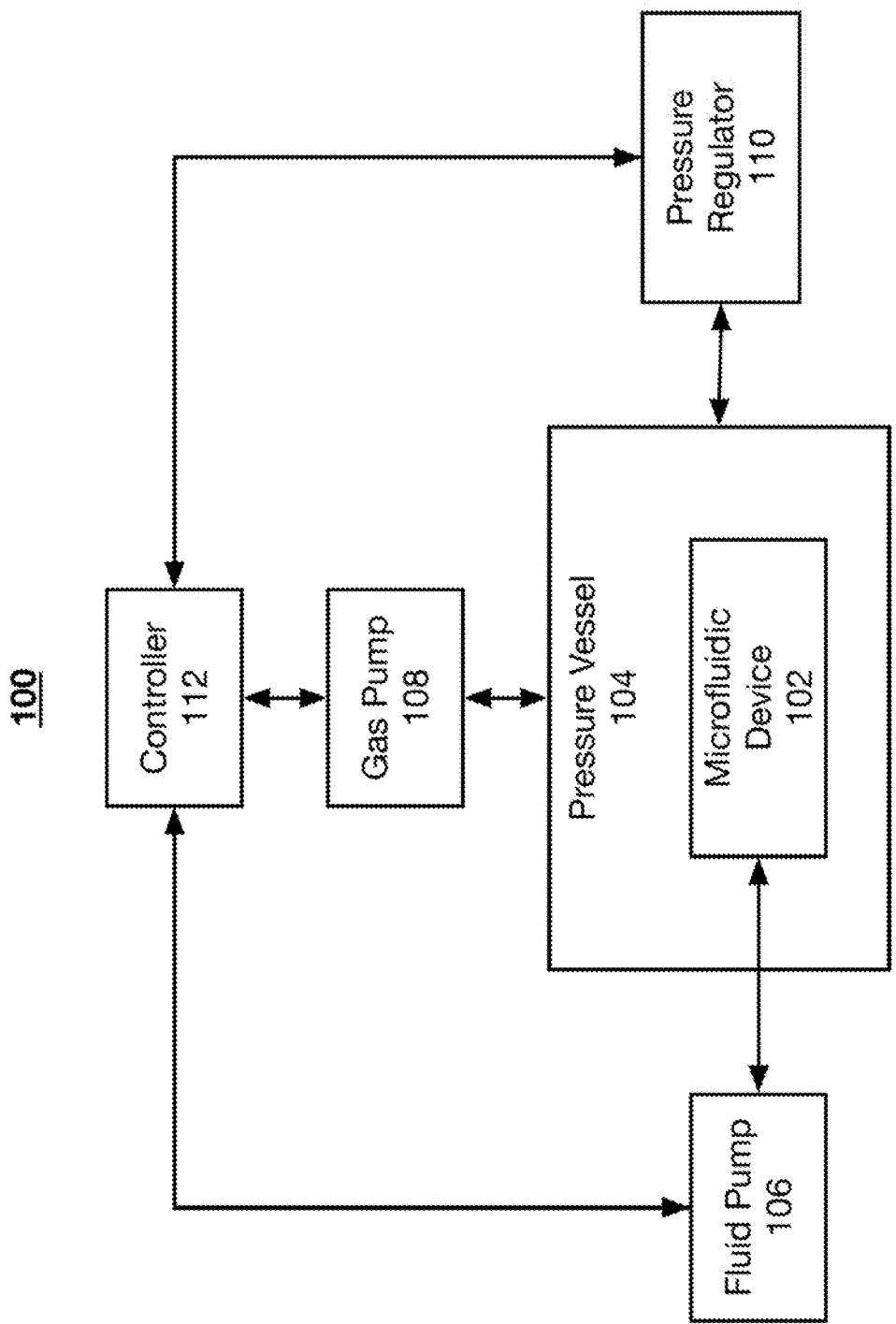
FIGS. 1A and 1B illustrate example systems that include a microfluidic device for the extraction of carbon dioxide from blood.

FIG. 1A illustrates an example system 100 that includes a microfluidic device 102 for the extraction of carbon dioxide from blood. As an overview, the system 100 includes a microfluidic device 102 that is housed within a pressure vessel 104. Fluid pump 106 flows a fluid (e.g., blood) through the microfluidic device 102. A gas pump 108 flows gas into the pressure vessel 104. One or more pressure regulators 110 regulate the pressure within the pressure vessel 104. The pumps 106 and 108 are controlled by a controller 112, which, in some implementations, receives pressure readings about the pressure vessel 104 from the pressure regulator 110. In other implementations, the gas pump 108 provides the gas to the gas channels of the microfluidic device 102 through a manifold, and the microfluidic device 102 is not housed within the pressure vessel 104.

In general, the microfluidic device 102 includes a plurality of polymer substrate layers. Each of the polymer substrate layers includes a plurality of gas channels and a plurality of fluid channels, which can also be referred to as blood channels. In some implementations, in each polymer substrate layer, the gas channels and fluid channels alternate such that each of the gas channels and each of the fluid channels (except for the channels on the edges of the polymer substrate layers) are between two fluid channels and two gas channels, respectively. The microfluidic device 102 is also configured such that each of the fluid channels of a first polymer substrate layer vertically aligns with and overlaps with a gas channel of a second polymer substrate layer. Similarly, each of the gas channels of the first polymer substrate layer vertically aligns with and overlaps a fluid channel of the second polymer substrate layer. This alignment configuration is referred to as a checkerboard configuration. In the checkerboard configuration, gas channels surround (e.g., are above, below, and on both sides) each interior fluid channel, and fluid channels surround each interior gas channel. In some implementations, the gas channels and fluid channels alternate according to a more complex alternation pattern without departing from the scope of the disclosure.

In other implementations, each of the channels in a given polymer substrate layer include the same type of channel. For example, gas layers that include only gas channels and fluid layers that include only fluid channels. In these implementations, the microfluidic device 102 includes stacked, alternating gas layers and fluid layers. Each of the layers is separated by a gas permeable membrane.

The microfluidic device 102 of the system can be housed within a pressure vessel 104. To reduce the complexity of a manifold system that routes gas to each of the gas channels of the microfluidic device 102, vents that supply gas to the gas channels of the microfluidic device 102 are open and exposed to the ambient, atmospheric conditions created within the pressure vessel 104. In these implementations, the gas channels do not require a complex manifold for the distribution of gas to each of the gas channels. In these implementations, only the fluid channels of the microfluidic device 102 are coupled to a manifold. The pressure vessel 104 is a pressure resistant housing that includes a hard shell configured to withstand elevated pressures. The pressure vessel 104 is manufactured from a gas impermeable plastic, such as polycarbonate, or a metal. The controller 112 controls the gas pump 108, which pumps gas, such as oxygen, into the pressure vessel 104 to pressurize the pressure vessel 104. In some implementations, the pressure vessel 104 is pressured to between about 1 atm to about 5 atm, between about 1 atm and about 4 atm, between 1 atm and about 3 atm, or between about 1.5 atm and about 2.5 atm.

The pressure vessel 104 of the system 100 includes one or more pressure regulators 110 to regulate the pressure within the pressure vessel 104 and maintain a predetermined pressure within the pressure vessel 104. In some implementations, the pressure regulator 110 includes pressure sensors that send pressure readings to the controller 112—enabling a closed loop control of the pressure within the pressure vessel 104. In some implementations, the pressure regulator 110 is a pressure release valve that prevents build-up of pressure substantially beyond the predetermined pressure. For example, the pressure regulator 110 may be a pressure valve that automatically opens when the pressure within the pressure vessel 104 reaches 2.5 atm. In operation, carbon dioxide diffuses out of the blood (e.g., through the polymer layers) and into pressure vessel 104. Venting the pressure within the pressure vessel 104 also enables the carbon dioxide to escape the pressure vessel 104, such that carbon dioxide levels do not build up within the pressure vessel 104.

The system 100 also includes a fluid pump 106 that is controlled by the controller 112 and configured to flow a fluid through the microfluidic device 102. For example, the fluid pump 106 is configured to flow blood through the fluid channels of the microfluidic device 102. The fluid pump 106 is fluidically coupled to a manifold of the microfluidic device 102 that distributes the fluid to each of the fluid channels of the microfluidic device 102. The fluid pump 106 is configured to flow a fluid through the microfluidic device 102 at a rate of between about 100 mL/min and about 1 L/min, between about 200 mL/min and about 800 mL/min, or between about 400 mL/min and about 600 mL/min.

In some implementations, the controller 112 controls, via the fluid pump 106 and the gas pump 108, the rate of gas flow and the gas composition entering the microfluidic 102 to increase carbon dioxide transfer rates out of the blood. For higher carrier gas flow rates, the removal of carbon dioxide increases, up to an asymptotic value. In some implementations, the system 100 modulates the carbon dioxide transfer rate by altering the carrier gas flow rate flowing through the gas channels of the microfluidic device 102. In some implementations, the composition of the carrier gas is substantially pure oxygen. When the carrier gas is substantially pure oxygen, the carbon dioxide transfer rate increases as the carrier gas flow rate is increased, up to an asymptotic value. This relationship is illustrated in the graph illustrated in FIG. 2.

In some implementations, the system 100 includes a plurality of microfluidic devices 102. The microfluidic devices 102 can be coupled together serially. Alternating microfluidic device 102 in the series of microfluidic device 102 can be configured to increase the amount of carbon dioxide transfer from the blood channels to the gas channels, with the other microfluidic device 102 configured to increase the amount of oxygen transferred from the gas channels to the blood channels. For example, a first microfluidic device can remove carbon dioxide from the blood and a second microfluidic device can oxygenate the blood. In some implementations, the microfluidic device described herein can be used to both oxygenate and to remove carbon dioxide from the blood flowing through the microfluidic device.

Figure 1B:
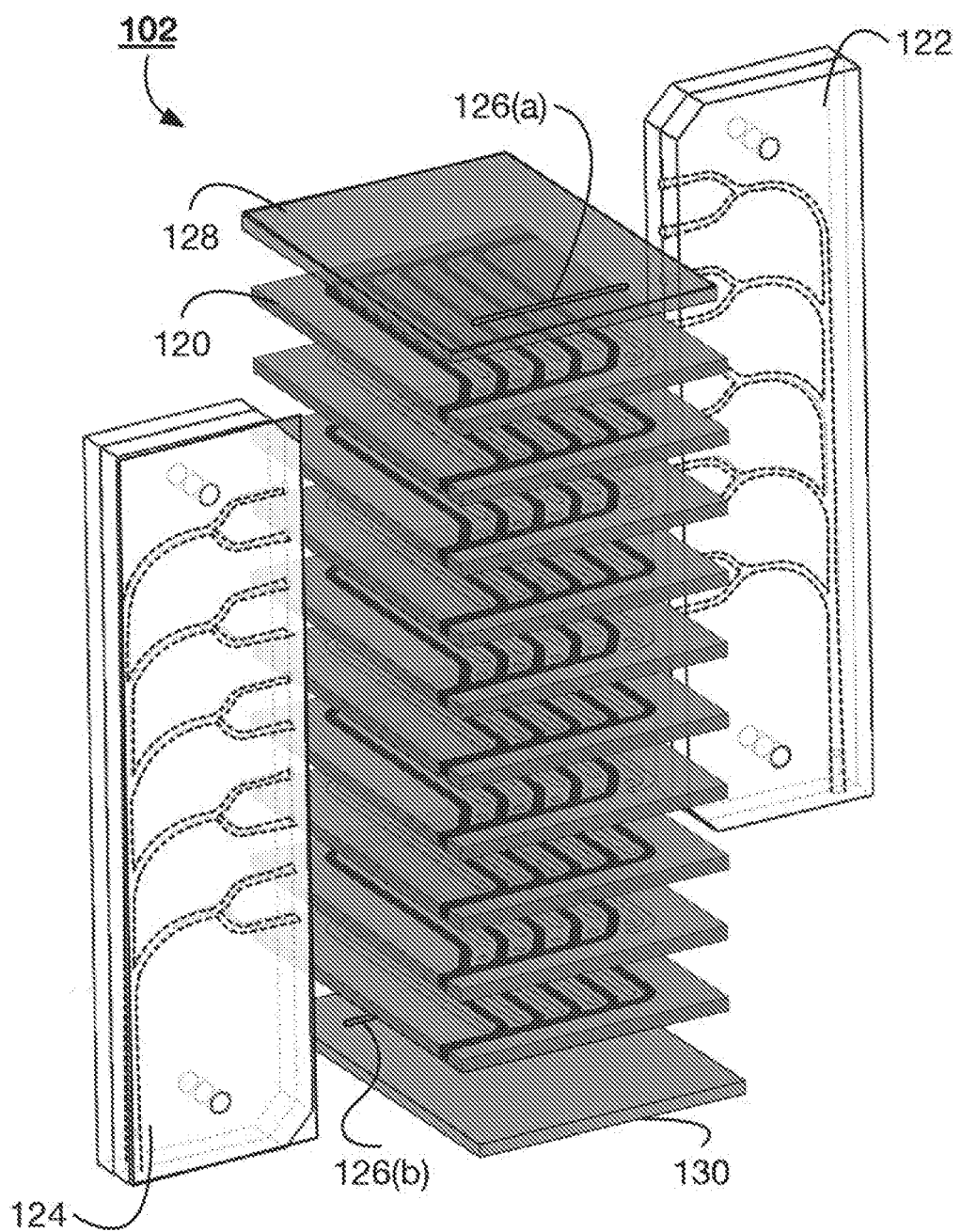

FIG. 1B illustrates an exploded view of an example microfluidic device 102 that can be used with the system 100 illustrated in FIG. 1. The microfluidic device 102 includes a plurality of polymer layers 120. The polymer layers 120 can alternate between including gas channels and blood channels. In some implementations, each of the polymer layers 120 can include a plurality of gas channels and a plurality of fluid channels. Neighboring polymer layers 120 can be separated from one another by a permeable membrane. The membrane can be a distensible membrane. The membrane can separate the gas channels in one layer from the blood channels in another layer. In some implementations, the membranes can form opposing walls of each of the gas and blood channels. For example, the floor and ceiling of each of the channels can be a membrane. In these implementations, the gas and blood channels are formed as longitudinal gaps in the polymer layers 120. This can give the microfluidic device 102 a repeating layer pattern of polymer layer 120, membrane, polymer layer 120, membrane. In other implementations, the gas and blood channels are formed as trenches within polymer layers 120. In these implementations, the polymer layer 120 can form the three walls of the channels and the membrane can form the fourth wall (e.g., the ceiling or floor). The microfluidic device 102 can include a repeating pattern of polymer layer 120, membrane, polymer layer 120. A variety of alternation patterns can be suitable for the system described herein.

The polymer layers 120 and membranes can be coupled together by clamping the layers together or by bonding the layers together with a glue or heat welding the layers together. Coupled together, the polymer layers 120 can create a separate fluid flow network and a separate gas flow network. In some implementations, the coupled polymer layers 120 create a fluid flow network and two separate gas flow networks.

The microfluidic device 102 can include a fluid inlet manifold 122 and a fluid outlet manifold 124. Fluid, such as blood, flows to each of the fluid channels of the different polymer layers 120 through the fluid inlet manifold 122. The fluid outlet manifold 124 collects the fluid as the fluid exits each of the polymer layers 120 (or the polymer layers 120 including the blood channels). The microfluidic device 102 includes vents 126(a) and 126(b) within the top layer 128 and bottom layer 130, respectively. In some implementations, the top layer 128 and bottom layer 130 do not include gas and fluid channels, and the vents 126 provide the inlets to the gas channels in the top most and bottom most polymer layers. That is, the gas channels can have open inlets that are exposed to the environment external to the microfluidic device 102. The vents provide access to the inlets of the gas channels to enable access to the ambient environment. The ambient environment can be the environment within the pressure vessel housing the microfluidic device 102. The vent 126(a) provides access to the gas channels of a first gas flow network and the vent 126(b) provides access to the gas channels of a second gas flow network. In some implementations, each polymer layer 120 that includes gas channels can include open inlets to enable ambient gas flow directly the gas channels of the respective polymer layers 120.

The inlet manifold 122 and the outlet manifold 124 can be configured to introduce and receive blood from each of the polymer layers 120 without causing substantial damage to the blood. For example, both the inlet manifold 122 and the outlet manifold 124 include gradual curving channels rather than right angles. In some implementations, the channels within the manifold mimic vascular channels. For example, the channels split at bifurcations. After a bifurcation, the size of the channel is reduced according to Murray's Law.

Each of the polymer layers 120 of microfluidic device 102 can be stacked upon one another such that the channels in a first polymer layer 120 substantially overlap and run parallel with the channels of polymer layers 120 on either side of the first polymer layer 120. In some implementations, the microfluidic device 102 includes between 10 and 100, between 30 and 80, or between 40 and 60 stacked polymer layers 120. The polymer layers 120 can include between about 25 and about 150 channels, between about 50 and about 125 channels, and between about 75 and about 100 channels.

In some implementations, the polymer layers 120 are manufactured from Poly(DiMethylSiloxane) (PDMS) and are directly stacked upon one another without a separate membrane between each of the polymer layers 120. For example, when the channels of the polymer layers 120 can be defined within a PDMS layer, oxygen can saturate from the gas channels and into the PDMS. The PDMS then serves as a source of oxygen for the fluid channels aligned horizontally and vertically with the gas channel. In other implementations, the polymer layers 120 are manufactured from thermoplastics, such as polystyrene, polycarbonate, polyimide, or cyclic olefin copolymer (COC), biodegradable polyesters, such as polycaprolactone (PCL), or soft elastomers such as polyglycerol sebacate (PGS). In these implementations, each of the polymer layers 120 can be separated from one another by a semi-porous membrane selected to permit diffusion of oxygen or other gas between the fluid channels and the gas channels.

Figure 2:
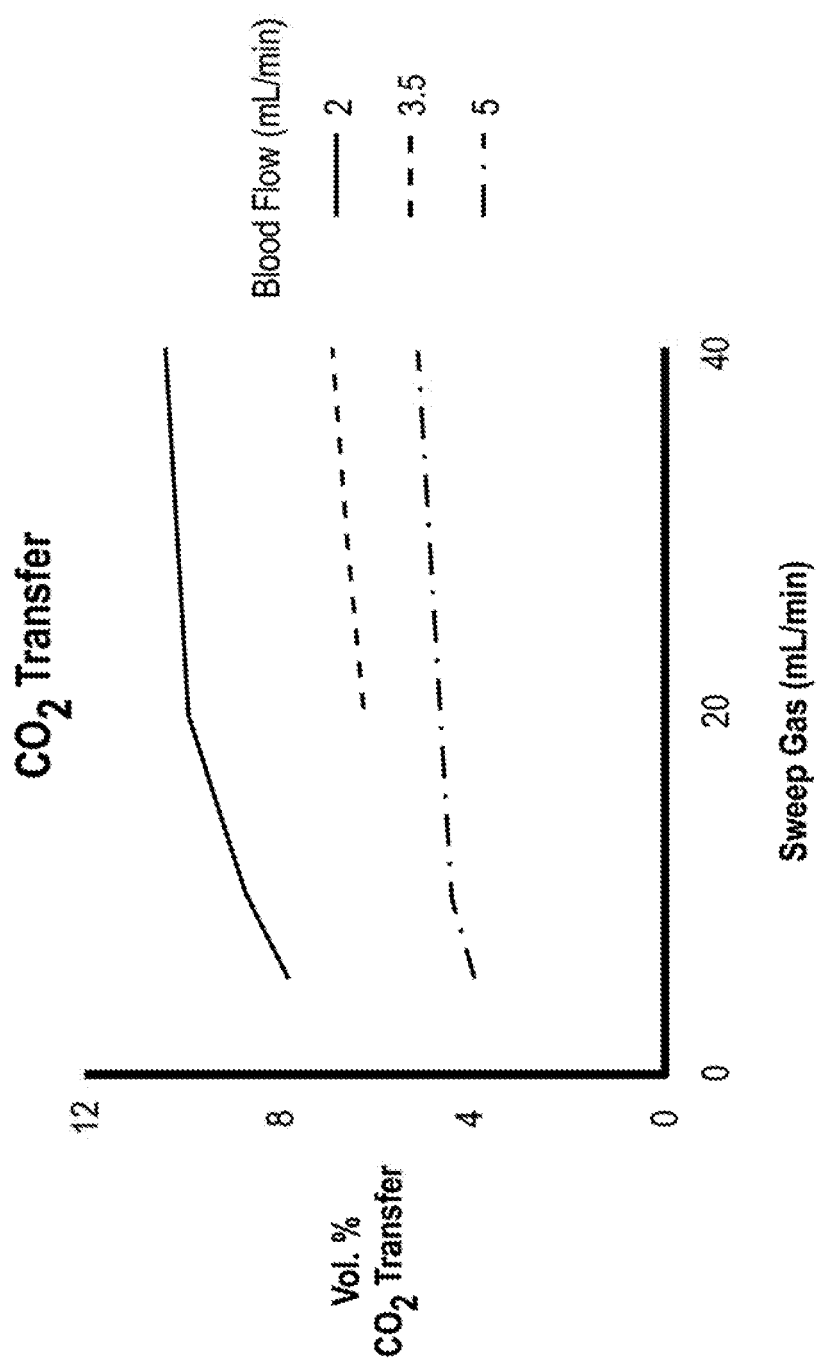
FIG. 2 illustrates a graph of the volume percent of carbon dioxide transfer versus the carrier gas flow rate.

FIG. 2 illustrates a graph of the volume percent of carbon dioxide transfer versus the carrier gas flow rate. The graph illustrates the relationship between the carbon dioxide transfer and the carrier gas flow rate for three different blood flow rates. In each experiment, the carrier gas was 100% oxygen. As illustrated in the graph, the transfer efficiency reaches an asymptotic value at 40 mL/min for all three blood flow rates, with the sharpest rise occurring between about 5 mL/min and about 10 mL/min blood flow rate.

Figure 3:
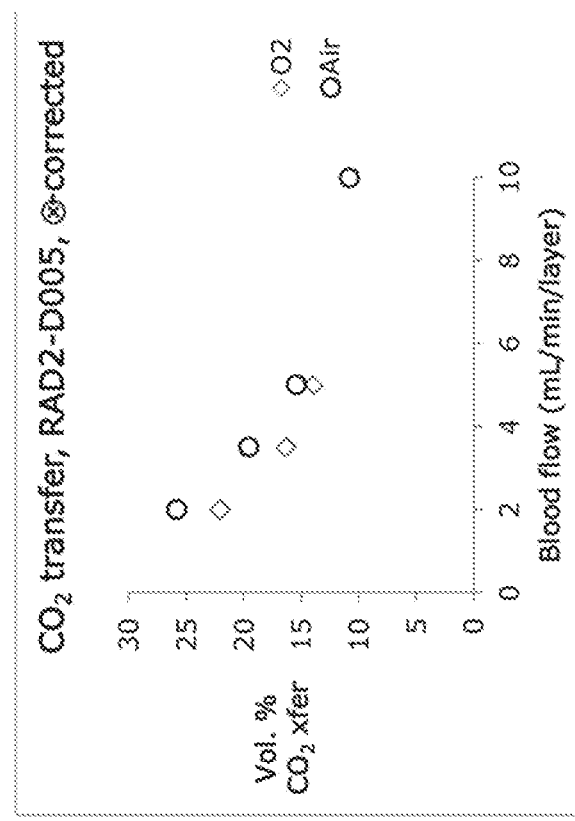
FIG. 3 illustrates a graph comparing carbon dioxide transfer using pure oxygen as the carrier gas versus air as the carrier gas.

In some implementations, the carrier gas includes a reduced oxygen concentration to increase the carbon dioxide transfer rate. FIG. 3 illustrates a graph comparing carbon dioxide transfer using pure oxygen as the carrier gas versus air as the carrier gas. The circles illustrate the volume percent transfer of carbon dioxide with respect to different blood flow rates using air as the carrier gas, and the diamonds illustrate the volume percent transfer of carbon dioxide with respect to different blood flow rates using pure oxygen as the carrier gas. As illustrated by the graph, the volume percent transfer of carbon dioxide is enhanced for several of the blood flow rates, indicating a boost in performance obtained by using air as the carrier gas. In other implementations, the carrier gas is pure nitrogen.

As illustrated in FIG. 3, carbon dioxide transfer rate is increased when the carrier gas is changed from pure oxygen to air. At some blood flow rates, the transfers are increased by as much as 20%. In some implementations, air can include a mixture of gasses. Air can be, by volume, about 20% oxygen, 78% nitrogen, with the remaining portion being a mix of other gases. In some implementations, the air (or other gas) can be dried or humidified based on the ambient conditions prior to use in the microfluidic devices described herein. The carrier gas can be pure oxygen or contain between about 10% and about 100%, between about 10% and about 75%, between about 10% and about 50%, or between about 10% and about 25% oxygen.

In some implementations, the blood channels of the microfluidic device include mixing elements to mix the blood as the blood flows along the length of the blood channels. In some implementations, the mixing elements can also disrupt boundary layers that can form along the blood side of the membrane. The mixing elements can be incorporated into a channel wall of the microfluidic device 102. The mixing elements can be included on one, two, or three walls of the channels. The mixing elements can also be included on a face of the membrane. The mixing elements can be distributed along the length of the blood flow channels. The mixing elements can mix the blood, such that blood near the floor of a channel is pushed toward the membrane. For example, under laminar flow conditions in a horizontal direction, there is little movement of the blood particles in a vertical direction. This can hinder the transfer of carbon dioxide across the membrane because the same portion of the blood remains near the membrane along the length of the channel. Under such circumstances, the amount of carbon dioxide in the blood near the membrane diminishes while the blood near the floor of the channel (e.g., the blood farthest away from the membrane) remains rich in carbon dioxide. The mixing elements push carbon dioxide rich blood towards the membrane from the floor of the blood channels.

The mixing elements can include a plurality of chevron-like mixing features disposed in a wall of the blood channels. The mixing elements can include other mixing elements such as ridges, channels, protrusions, or a combination thereof. Mixing elements formed in the membrane or walls of the blood channels can be referred to as passive mixing elements. The mixing elements can be spread along substantially the entire length of a blood channels. In other implementations, the mixing elements cover only a sub-portion of the total length of the blood channels. In yet other implementations, the mixing elements can be grouped together. For example, the blood channels can include a first type of mixing element along a first portion of the channels and then a second type of mixing element along a second portion of the channels. The distribution of the mixing elements can be equal along the length of the channels. Or, the distribution of the mixing elements can change along the length of the channels. For example, channels can include a higher density of mixing elements towards the outlet end of the channels when compared to the inlet end.

In some implementations, the height or depth of the mixing elements is between about 5% and about 10%, between about 10% and about 20%, or between about 20% and 30% of the total height of the blood channels. In some implementations, each of the mixing elements in a channel is the same height or depth. While, in other implementations, the height or depth of the mixing elements changes along the length of the channel. The blood and gas channels of the microfluidic device can be between about 100 μm and about 500 μm, between about 150 μm and about 450 μm, between about 200 μm and about 400 μm, and between about 200 μm and about 350 μm deep.

In some implementations, the mixing elements are dynamic. The mixing elements can be formed by the distension of the membrane toward (or away from) the central, longitudinal axis of the respective blood channels. In some implementations, the gas pump 108 is configured to enhance mixing of the blood, and to increase carbon dioxide transfer, by supplying pulsed mechanical waves of gas to the gas channels that modulate the channel geometry in an oscillatory fashion. The increased pressure within the gas channels causes the membrane to distend toward the central, longitudinal axis of the respective blood channels. In some implementations, the flow of blood can be pulsed to generate pressure waves through the blood channels that distend the membrane and cause oscillations in the blood channels' geometry. In some implementations, the microfluidic device can include a mixture of passive and dynamic mixing elements. For example, the floor of the blood channels can include chevron mixing elements and a pulsed gas flow can be used to distend the membrane in an oscillatory fashion to modulate the blood channels' geometry (e.g., the shape of the cross-sectional area).

In other implementations, the blood is supplied to the blood flow channels in a pulsatile fashion to modulate the channel geometry. In these implementations, the pressure of the blood flowing through the blood channels can distend the membrane away from the central, longitudinal axis of the respective blood channels.

Figure 4A:
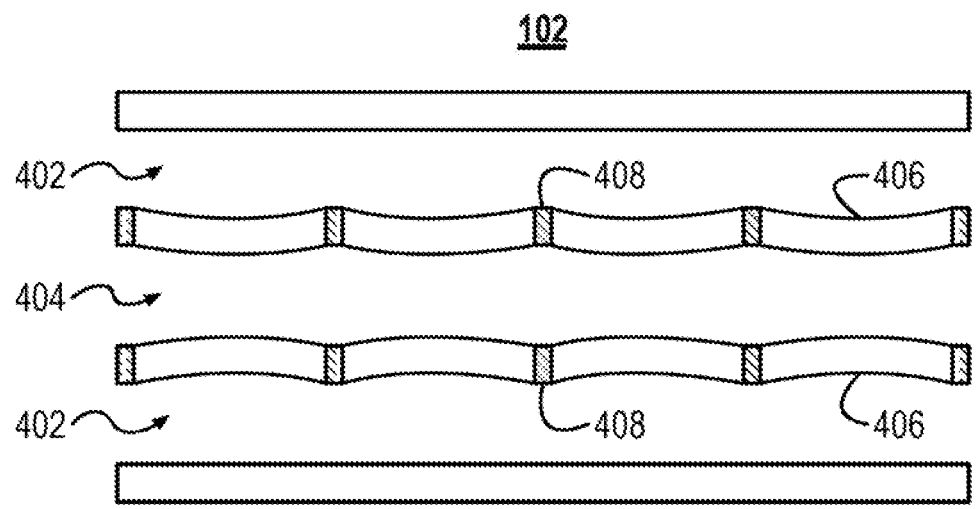
FIGS. 4A-4E illustrate a cross-sectional views of example microfluidic devices that are configured to modulate the channel geometry in an oscillatory fashion for use in with the system illustrated in FIG. 1A.

FIG. 4A illustrates a cross-sectional view of an example microfluidic device 102 configured to modulate the channel geometry in an oscillatory fashion. The microfluidic device 102 includes two gas channels 402 and a blood channel 404. The blood channel 404 is separated from each of the gas channels 402 by a respective membrane 406. The membranes 406 include a plurality of support structures 408, which can also be referred to as ribs 408.

Also referring to FIG. 1, gas flows through the gas channels 402 in a pulsatile manner. The controller 112 controls the pulsatile pressure of the gas flowing through the gas channels 402. The controller 112 can flow the gas through the gas channels 402 at a rate between about 10 cycles/min to about 30 cycles/min, between about 15 cycles/min to about 25 cycles/min, or between about 15 cycles/min to about 20 cycles/min.

During a cycle of relatively high pressure, as illustrated in FIG. 4, the high gas pressure distends the membrane 406 toward the central axis of the blood channel 404, which temporarily constricts the blood channel 404. As illustrated, the support structures 408 keep the membrane stationary and the membrane 406 distends between the support structures 408. When the gas flow cycles to a relatively low pressure (e.g., a pressure less than or equal to the pressure of the blood in the blood channel 404), the membrane 406 returns to its original position. When the gas pressure causes the membrane 406 to distend toward the central axis of the blood channel 404, a shape of the blood channel's cross-sectional area changes along the length of the blood channel. For example, in the example illustrated in FIG. 4A, the blood channel 404 is the widest at the cross-sections taken at one of the support structures 408. The blood channel 404 is the narrowest at the cross-sections taken half way between neighboring support structures 408. As illustrated the changing shape of the channel's cross-sectional area along the length of the blood channel 404 can be one form of oscillation. The shape of the cross-sectional area can also oscillate from default position (where the membrane 406 is not distended) to the constricted (or dilated) positions where the membrane 406 is distended toward (or away) from the blood channel's central axis.

In some implementations, the blood is flowed through the blood channel 404 with a pulsatile waveform. The pulsatile waveform may mimic the hemodynamic waveform of the cardiac pumping of blood in the body. Pulsation of the blood can be generated using a shuttle pump.

The distension of the membrane 406 creates small undulations in the surface of the membrane 406 facing the blood channel 404. The undulations can appear in an oscillatory fashion with the pulsatile gas flow. The undulations can provide a natural means to disturb and disrupt boundary layers along the membrane 406. The undulations also mix the blood and stir the carbon dioxide remaining in the blood to enhance mixing and transfer.

As illustrated in FIG. 4A, the support structures 408 are embedded within the membrane 406 of the microfluidic device 102. The membranes described herein can be between about 50 µm and about 200 µm, between about 50 µm and about 150 µm, or between about 50 µm and about 100 µm.

In some implementations, the ribs are distributed evenly along the length of the plurality of gas channels. For example, the distance between neighboring ribs can be constant along the length of the gas channels. In other implementations, the ribs are distributed unevenly along the length of the plurality of gas channels. For example, the distance between neighboring ribs can change along the length of the gas channels. The ribs can be more tightly spaced toward the outlet of the gas channels, can be more tightly spaced toward the inlet of the gas channels, or the distribution of the ribs can be random.

Figure 4B:
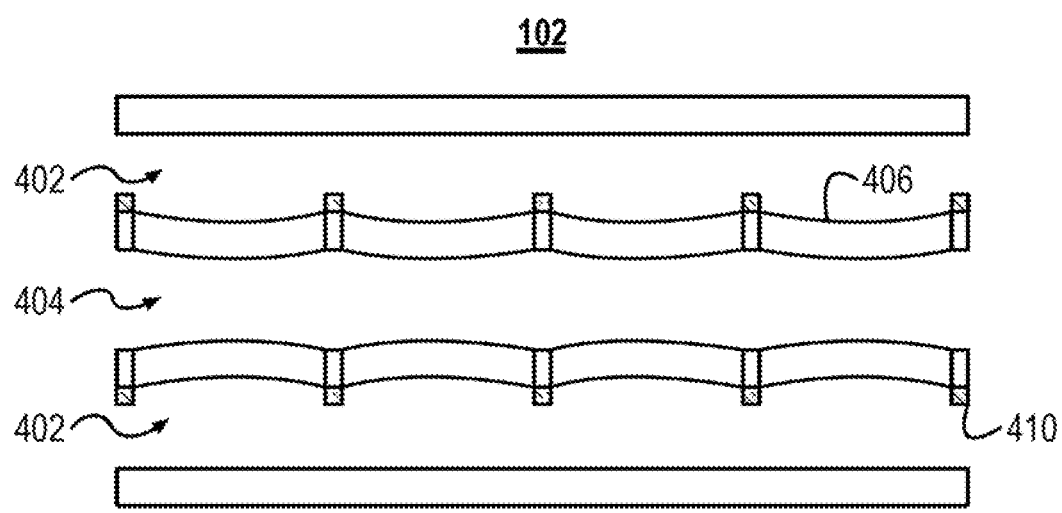

In other implementations, the support structures 408 are not embedded within the membrane 406. For example, FIG. 4B illustrates a microfluidic device 102 that includes support structures 410 that are coupled to the gas channel surface of the membranes 406. The support structure 408 can include a material that is stiffer than the material of the membrane 406. In some implementations, the support structure 408 can be manufactured in PDMS that has a different composition than the PDMS of the membrane 406 to make the support structure 408 stiffer than the membrane 406.

Figure 4C:
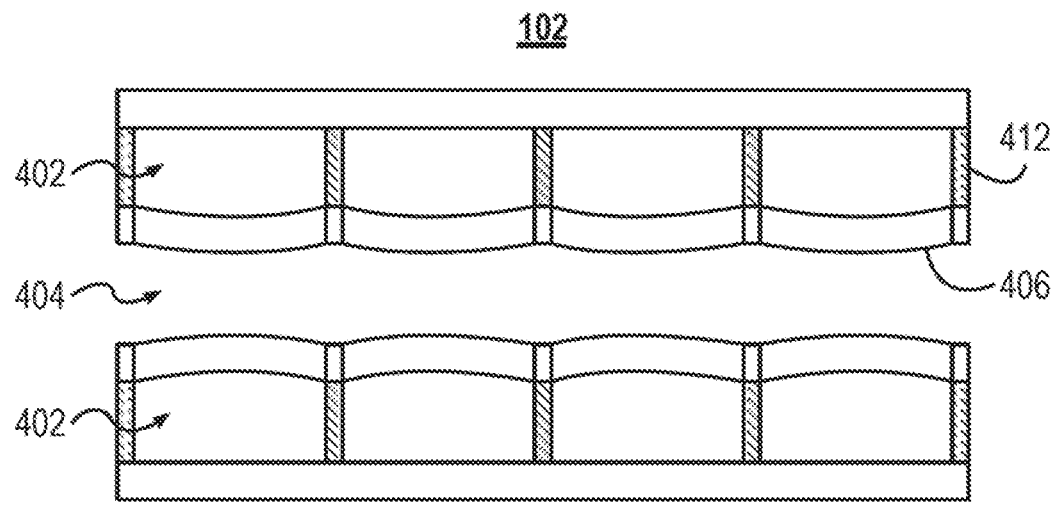

FIG. 4C illustrates a microfluidic device that includes support structures that are posts 412. The posts 412 are another example of a support structure that are coupled to the gas surface of the membranes 406. The posts 412 enable gas to flow along the length of the gas channels 402. The posts 412 couple a portion of the membrane 406 to an opposite wall of the gas channels 402. The posts 412 substantially prevent the membranes 406 from flexing near the portion of the membrane 406 where they are coupled.

Figure 4D:
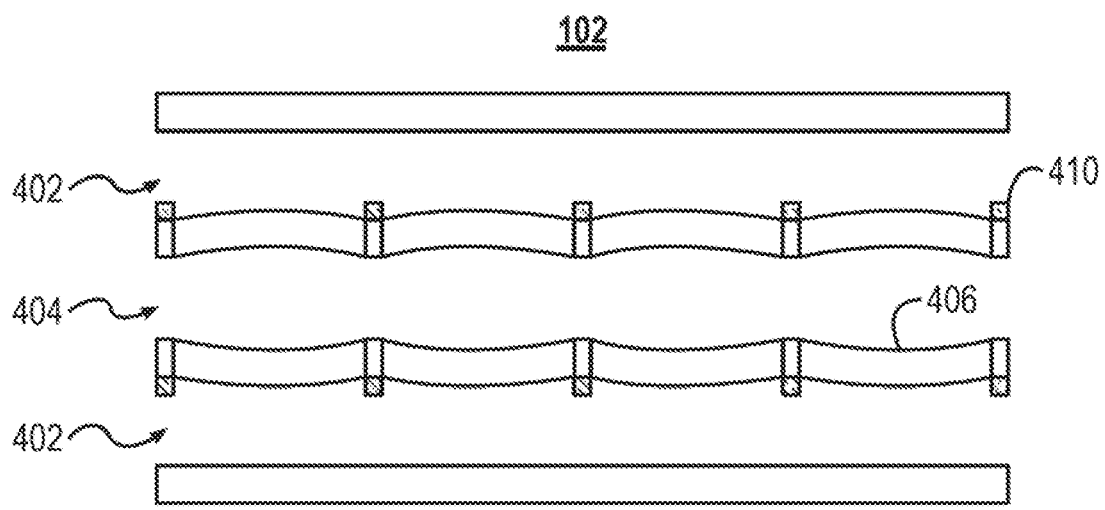

FIG. 4D illustrates a microfluidic device 102. The microfluidic device 102 includes support structures 410, similar to those described above in relation to FIG. 4B. The microfluidic device 102 illustrates one example where blood flows through the blood flow channels 404 in a pulsatile manner. The pulsatile flow of the blood causes the membranes 406 to flex outward toward the gas channels 402.

In some implementations, the support structures of the microfluidic device can be any of the support structures described herein or a combination thereof. Additionally, the support structures can include a mesh that spans a surface of the membrane 406. The ribs, bars, or meshes can include a metal or a plastic that is stiffer than the membrane 406.

Figure 4E:
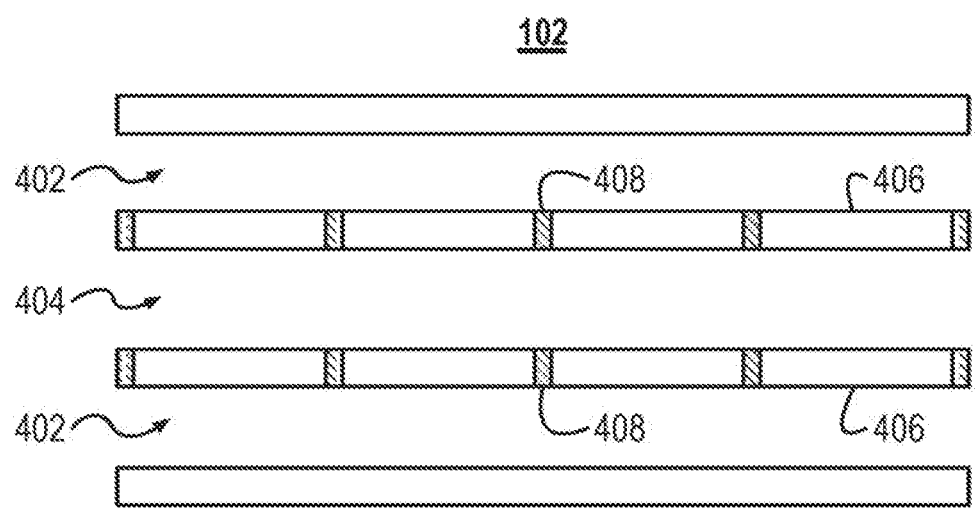

FIG. 4E illustrates a microfluidic device 102. The microfluidic device 102 illustrated in FIG. 4E is similar to the microfluidic device 102 illustrated in FIG. 4A. As illustrated in FIG. 4E, the membranes 406 are not distended toward the blood channel 404. For example, the pressure within the gas channels 402 may not be great enough to force a deflection of the membrane 406. In some implementations, the pulsatile flow in the gas channels 402 can cause the cross-sectional area to oscillate between the cross-sectional area illustrated in FIG. 4E and the cross-sectional area illustrated in FIG. 4A. The shape of the cross-sectional area can oscillate over time (e.g., the membrane can distend and then recover). The shape of the cross-sectional area can also oscillate over a distance. For example, as illustrated in FIG. 4A, the pressurized gas channels 402 cause the cross-sectional area of the blood channel 404 to change in a sinusoidal fashion. That is, at least one of the height or width of the blood channel 404 changes in a sinusoidal fashion along the length of the blood channel 404. In other implementations, the shape of the cross-sectional area can oscillate in a non-sinusoidal fashion. The shape of the cross-sectional area can also oscillate over both over time and distance (such as when a pulsatile gas flow causes the microfluidic device 102 to oscillate between the state illustrated in FIG. 4A and FIG. 4E.

Figure 5:
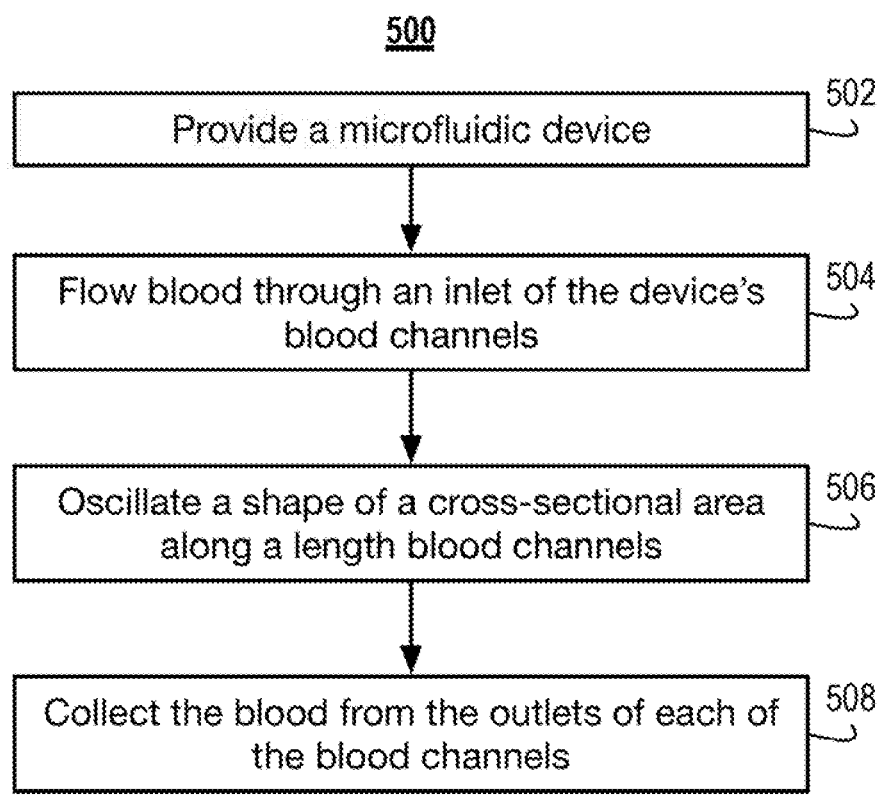
FIG. 5 illustrates a block diagram of an example method of removing carbon dioxide from blood using the system illustrated in FIG. 1A.

FIG. 5 illustrates a block diagram of an example method 500 of removing carbon dioxide from blood. The method 500 can include providing a microfluidic device (ACT 502). The method 500 can include flowing blood through an inlet of the device's blood channels (ACT 504). The method 500 can include oscillating a shape of a cross-sectional area along a length of the device's blood channels (ACT 506). The method 500 can include collecting the blood from the outlet of the device's blood channels (ACT 508).

As set forth above, the method 500 can include providing a microfluidic device (ACT 502). The microfluidic device can be any of the microfluidic devices described herein. The microfluidic device can include multiple polymer layers. A first layer can include a plurality of gas channels. A second layer can include a plurality of blood channels. The blood and gas channels can be separated from one another by a distensible membrane coupled between the layers. The plurality of blood channels can include a cross-sectional area defined in the second layer. In the default state (or initial state) the cross-sectional area can be substantially uniform along the length of the blood channels. The blood channels can be fluid channels that are capable or otherwise configured to flow fluids in addition to or in place of blood.

The method 500 can include flowing blood through an inlet of the device's blood channels (ACT 504). In some implementations, the blood channels are coupled with a manifold system. The blood can be flowed through an inlet manifold coupled with the inlet of each of the plurality of blood channels. The manifold can include channels with smooth and gradual bifurcations and bends that can reduce trauma to the blood. In some implementations, the gas channels are coupled to a gas manifold. In other implementations, the gas channels are not coupled to a gas manifold. The gas channels' inlets can be open to expose the gas channels to the ambient environment.

The method 500 can include oscillating a shape of a cross-sectional area along a length of the device's blood channels (ACT 506). Oscillating the shape of the cross-sectional area along the length of the device's blood channels can include changing the cross-sectional area in a pulsatile manner (e.g., constricting and then relaxing the blood channels), changing the cross-sectional area along the length of the blood channels (e.g., constricting the blood channels at points along the length of the blood channels), or a combination thereof (e.g., constricting the blood channels at points in a pulsatile manner).

The shape of the cross-sectional area can be changed by distending the membrane into the blood channels. The membrane can be distended into the blood channels by pressurizing the gas channels. When the pressure in the gas channels is greater than the pressure in the blood channels, the membrane can distend into the blood channels. In some implementations, the membrane can be distended into the gas channels.

In some implementations, the microfluidic device is placed into a pressure vessel. The inlets to the device's gas channels can be open to the ambient environment such that the pressure within the gas channels is substantially that of the pressure within the pressure vessel. By pressurizing the pressure vessels, the gas channels pressurize and distend the membrane. The level of pressure in the pressure vessel can be controlled to be greater than or less than the pressure of the blood within the blood channels. The gas can be flowed through the gas channels with a pulsatile flow. The pulsatile flow can be generated by oscillating the pressure within the pressure vessel between a relatively low and a relatively high-pressure value. The relatively low pressure can be a pressure less than or about equal to the pressure within the blood channels and the relatively high pressure can be a pressure greater than the pressure in the blood channels. The pressure controls the amount the membrane distends. The membrane distension can control the shape of the cross-sectional area of the blood channels. The amount of the membrane's distension can be relative to the gas pressure of the gas in the plurality of gas channels.

The method 500 can include collecting the blood from the outlet of the device's blood channels (ACT 508). The outlets of the blood channels can be coupled with an outlet manifold. The outlet manifold can collect the blood exiting the blood channels without causing damage to the blood. In some implementations, the blood exiting the microfluidic device can be passed to an oxygenator device that can oxygenate the blood. In other implementations, the blood can pass through an oxygenator prior to entry into the microfluidic device.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, an intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

As used herein in the specification and in the claims, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents. All publicly available documents referenced herein, including but not limited to U.S. patents, are specifically incorporated by reference.

What is claimed:

1. A microfluidic flow device comprising:
   a plurality of first layers comprising a plurality of gas channels to permit gas to flow through the microfluidic flow device;
   a plurality of distensible membranes wherein each membrane of the plurality of distensible membranes is coupled to a respective gas channel of the plurality of gas channels and is distensible in response to pressurization;
   a plurality of supports at least partially embedded within a membrane of the plurality of distensible membranes, the plurality of supports distributed such that the membrane is supported at intervals along a length of the membrane, wherein the plurality of supports are disposed to reduce flexure at a portion of the membrane; and
   a plurality of second layers comprising a plurality of blood channels and coupled respectively with the plurality of distensible membranes,
   the plurality of supports comprising supports each having (i) a first end exposed to the respective gas channel of the plurality of gas channels and (ii) a second end exposed to a respective blood channel of the plurality of blood channels, the supports extending from the first end to the second end in a direction perpendicular to a flow direction in which gas flows in the respective gas channel and perpendicular to a direction in which blood flows in the respective blood channel,
   the plurality of blood channels separated from the plurality of gas channels by the plurality of distensible membranes, and configured to permit blood to flow through the microfluidic flow device, the plurality of blood channels comprising:
      a cross-sectional area defined in each of the plurality of second layers, a shape of the cross-sectional area configured to oscillate by application of gas pressure such that each respective blood channel varies between a first width and a second width, wherein gas is supplied to the plurality of gas channels such that a gas flow is at a rate between about ten cycles per minute to about thirty cycles per minute,
      wherein the plurality of first layers, the plurality of distensible membranes and the plurality of second layers are stacked in an alternating arrangement such that a respective membrane is provided between a respective first layer and a respective second layer.

2. The device of claim 1, further comprising:
   an inlet manifold coupled with an inlet of each of the plurality of blood channels;
   an outlet manifold coupled with an outlet of each of the plurality of blood channels; and
   the plurality of gas channels comprising an open inlet end and an open outlet end.

3. The device of claim 1, further comprising:
   a pressure vessel housing the plurality of first layers and the plurality of second layers, wherein the pressure vessel is configured to flow the gas into an open end of each of the plurality of gas channels.

4. The device of claim 1, wherein the shape of the cross-sectional area is controlled by a degree of distension of at least one of the plurality of distensible membranes.

5. The device of claim 1, wherein at least one of the plurality of distensible membranes is configured to deform a distance responsive to a gas pressure of the gas in the plurality of gas channels.

6. The device of claim 1, wherein the supports differ in material from the plurality of distensible membranes, and the shape of the cross-sectional area deflects between each of the plurality of supports.

7. The device of claim 6, wherein the supports are distributed evenly along the length of the plurality of gas channels.

8. The device of claim 6, wherein the supports are distributed unevenly along the length of the plurality of gas channels.

9. The device of claim 1, wherein the supports are stiffer than the plurality of distensible membranes and extend from the membrane and into the respective gas channel of the plurality of gas channels.

10. A method of removing carbon dioxide from blood, comprising:
    providing a microfluidic device comprising:
       a plurality of first layers comprising a plurality of gas channels;
       a plurality of distensible membranes wherein each membrane of the plurality of distensible membranes is coupled to a respective gas channel of the plurality of gas channels; and
       a plurality of supports at least partially embedded within a membrane of the plurality of distensible membranes, the plurality of supports distributed such that the membrane of the plurality of distensible membranes is supported at intervals along a length of the membrane, wherein the plurality of supports are disposed to reduce flexure at a portion of the membrane;
       a plurality of second layers comprising a plurality of blood channels and coupled respectively with the plurality of distensible membranes,
       the plurality of supports comprising supports each having (i) a first end exposed to the respective gas channel of the plurality of gas channels and (ii) a second end exposed to a respective blood channel of the plurality of blood channels, the supports extending from the first end to the second end in a direction perpendicular to a flow direction in which gas flows in the respective gas channel and perpendicular to a direction in which blood flows in the respective blood channel,
       the plurality of blood channels separated from the plurality of gas channels by the plurality of distensible membranes, the plurality of blood channels having a cross-sectional area defined in each of the plurality of second layers;
    flowing blood through into an inlet of each of the plurality of blood channels;
    oscillating a shape of the cross-sectional area such that each respective blood channel varies between a first width and a second width by pressurizing, with a gas, the plurality of gas channels to distend the plurality of distensible membranes and enhance transfer of the carbon dioxide so as to remove the carbon dioxide from the blood; and
    collecting the blood from an outlet of each of the plurality of blood channels,
    wherein the plurality of first layers, the plurality of distensible membranes and the plurality of second layers are stacked in an alternating arrangement such that a respective membrane is provided between a respective first layer and a respective second layer, and wherein pressurizing the plurality of gas channels comprises supplying the gas such that a gas flow is at a rate between about ten cycles per minute to about thirty cycles per minute.

11. The method of claim 10, further comprising:
flowing the blood through an inlet manifold coupled with the inlet of each of the plurality of blood channels;
collecting, from an outlet manifold coupled with the outlet of each of the plurality of blood channels, the blood; and
flowing the gas into an open inlet end of the plurality of gas channels.

12. The method of claim 10, further comprising pressurizing a pressure vessel housing the microfluidic device.

13. The method of claim 10, further comprising flowing blood through the plurality of blood channels with a pulsatile flow.

14. The method of claim 10, wherein the shape of the cross-sectional area is controlled by a degree of distension of the plurality of distensible membranes.

15. The method of claim 10, wherein each of the plurality of distensible membranes is configured to deform a distance responsive to a gas pressure of the gas in the plurality of gas channels.

16. The method of claim 10, wherein the supports differ in material from the plurality of distensible membranes, and the method further comprises distending the plurality of distensible membranes between the supports.

17. The method of claim 16, wherein the supports are distributed evenly along the length of the plurality of gas channels.

18. The method of claim 16, wherein the supports are distributed unevenly along the length of the plurality of gas channels.

19. The method of claim 10, wherein the supports are stiffer than the plurality of distensible membranes extend from the membrane and into the respective gas channel of the plurality of gas channels.

20. The method of claim 10, wherein the gas is air.

* * * * *